United States Patent [19]

Nutt et al.

[11] Patent Number: 5,340,798
[45] Date of Patent: Aug. 23, 1994

[54] FIBRINOGEN RECEPTOR ANTAGONISTS

[75] Inventors: Ruth F. Nutt, Green Lane; Daniel F. Veber, Ambler, both of Pa.

[73] Assignee: Merck & Co., Inc., Rahway, N.J.

[21] Appl. No.: 961,221

[22] Filed: Oct. 14, 1992

[51] Int. Cl.$^5$ .................. A61K 37/00; A61K 37/02; C07K 5/00; C07K 7/00
[52] U.S. Cl. .................................... 514/18; 514/19; 530/330; 530/331
[58] Field of Search ............. 514/18, 19; 530/330, 530/337

[56] References Cited

U.S. PATENT DOCUMENTS 4,064,255 12/1977 Champseix et al. .
5,064,814 11/1991 Klein et al. .

FOREIGN PATENT DOCUMENTS 0352249 7/1989 European Pat. Off. .
0372486 12/1989 European Pat. Off. .
0381033 1/1990 European Pat. Off. .
0384362 2/1990 European Pat. Off. .
0405537 6/1990 European Pat. Off. ... C07D 209/20
0478328 9/1991 European Pat. Off. ... C07C 271/22
0478362 9/1991 European Pat. Off. .
0478363 9/1991 European Pat. Off. ... C07D 211/22
0479481 9/1991 European Pat. Off. ....... C07K 5/10

Primary Examiner—Lester L. Lee
Assistant Examiner—C. A. Salata
Attorney, Agent, or Firm—Richard S. Parr; Melvin Winokur; Paul D. Matukaitis

[57] ABSTRACT

The present invention comprises fibrinogen receptor antagonist compounds, compositions containing them and methods for using them to inhibit fibrinogen binding to blood platelets. Compounds of the invention have the following formula

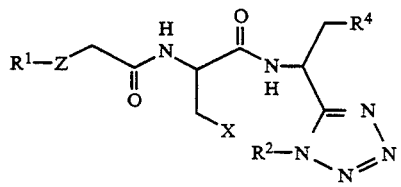

wherein Z is

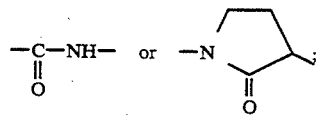

X is COOH, CH$_2$SH or SH;
R$^1$ is Y—R$^3$, wherein R$^3$ is alkyl and Y is amino, pyridinyl, pyrimidinyl or piperidinyl;
R$^2$ is H, alkyl, aryl, or arylalkyl; and
R$^4$ is alkyl, heteroalkyl, aryl or heteroaryl, wherein the aryl or heteroaryl group can be mono- or bicyclic.

An exemplary compound of the invention is

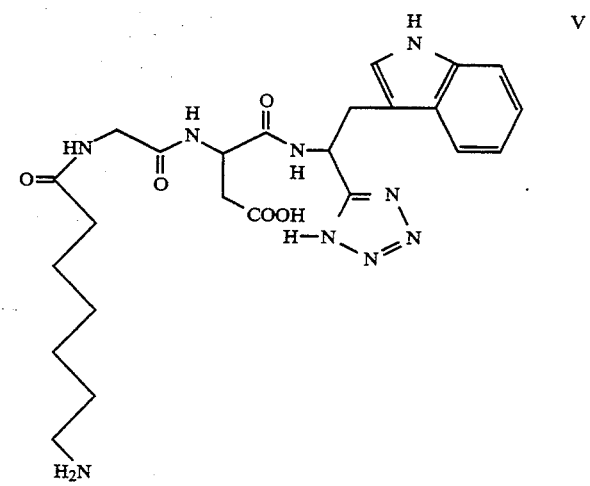

4 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothethial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578.079.

Ruggeri et al., Proc. Nat'l Acad. Sci. U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 ( 1984); Ginsberg et al., J. Biol. Chem. 260(7), 3931–3936 (1985); and Haverstick et al., Blood 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gpIIb/IIIa complex. For example, Huang et al., J. Biol. Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. USA, 87, 2471–2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a disulfide linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood.

The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$—A—(W-)$_a$—X—(CH$_2$)$_b$—(Y)$_c$—B—Z—COOR wherein $R^1$ is a guanidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. In addition, these compounds, by virtue of a tetrazole group replacing a C-terminal carboxyl group are less susceptible to metabolism by certain proteases present in the GI tract as well as elsewhere in the body. The compounds show in vivo activity after oral administration as a consequence of this increased metabolic stability. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

Compounds of the invention are those having four structural elements: A) amino group of pKa>6, B) a carboxy or thiol group, C) a hydrogen, lower alkyl, heteroalkyl, aromatic, or heteroaromatic group, D) a 5-substituted tetrazole, and E) a nitrogen group, carbocyclic group, heterocyclic group, carboaromatic group, aromatic, or heteroaromatic group which does not reduce the pKa of A below 6 and which creates a distance between groups A and B such that good binding to the fibrinogen receptor can be maintained, i.e. 10–25 ÅA, preferably 15–20 Å. These structural elements influence the ability of compounds of the invention to bind to the protein complex IIb-IIIa and inhibit platelet aggregation. These structural elements are spacially arranged according to the following general structure:

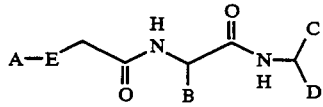

Preferably, the present invention comprises fibrinogen receptor antagonist compounds, compositions containing them and methods for using them to inhibit fibrinogen binding to blood platelets. Compounds of the invention have the following formula

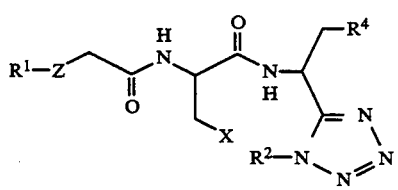

wherein

X is COOH, CH$_2$SH or SH;
$R^1$ is

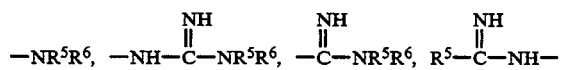

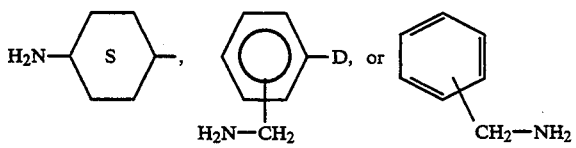

where D = $-\overset{O}{\underset{\|}{C}}-$, $-S(O)_q$, or $-O-$;

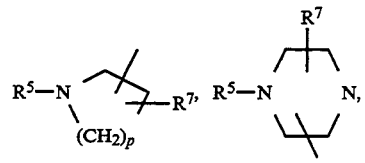

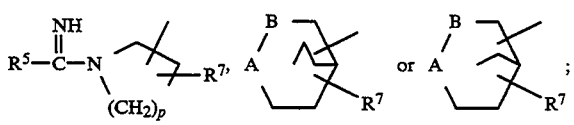

where A=N and B=—CH$_2$—, or A=—CH— and B=NR$^5$;

$R^5$, $R^6$ and $R^7$ are independently hydrogen,
C$_{1-12}$ alkyl, unsubstituted or substituted, with one or more C$_{1-6}$ alkyl groups,
arylC$_{0-4}$ alkyl, or cyano,
provided that when $R^5$ and $R^6$ are independently cyano, $R^1$ is

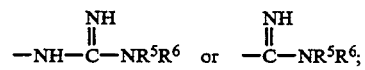

Z is

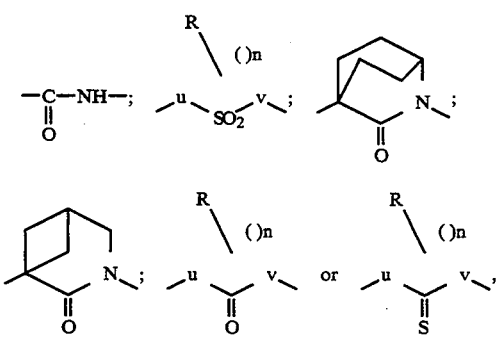

wherein n=0–5
u is —CH—, —C—, or —N—;
v is —CH—, —C—, or —N—;
p is 1–6; and
q is 0–2,
or the pharmaceutically acceptable salts thereof, or optical isomers thereof.

The invention is not to be considered as limited to racemates and mixtures, but also to encompass the individual S and R optical isomers of the compounds, and pharmaceutically acceptable salts thereof.

DETAILED DESCRIPTION OF THE INVENTION

Preferably, compounds of the invention have the formula

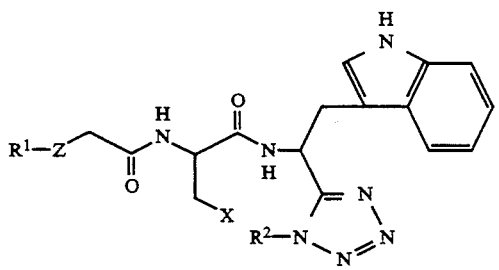

wherein Z is

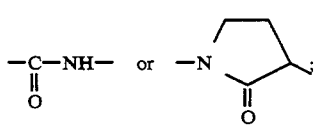

X is COOH, CH$_2$SH or SH;
R$^1$ is Y—R$^3$, wherein R$^3$ is alkyl and Y is amino, pyrimidinyl or piperidinyl; and
R$^2$ is H, alkyl, aryl, or arylalkyl.

More preferred compounds of the invention are those having the formula

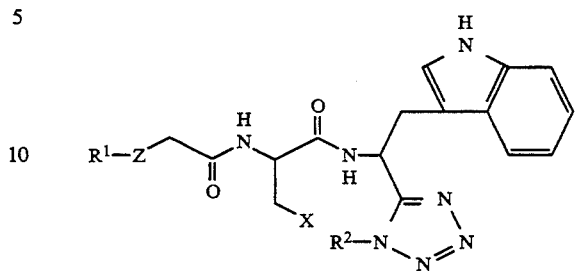

wherein Z is

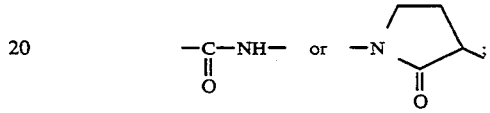

X is COOH;
R$^1$ is Y—R$^3$, wherein R$^3$ is alkyl and Y is amino or piperidinyl; and
R$^2$ is H or alkyl.

Most preferred compounds of the present invention are the following:

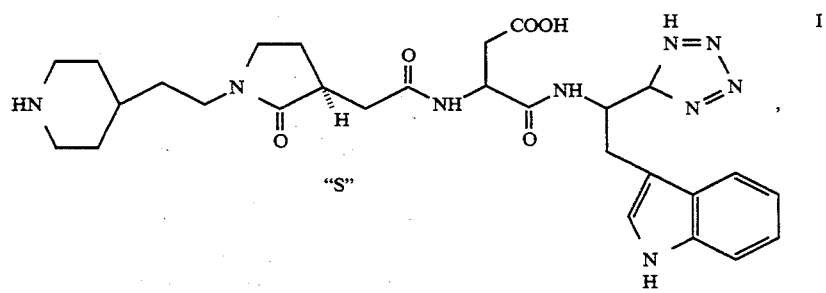

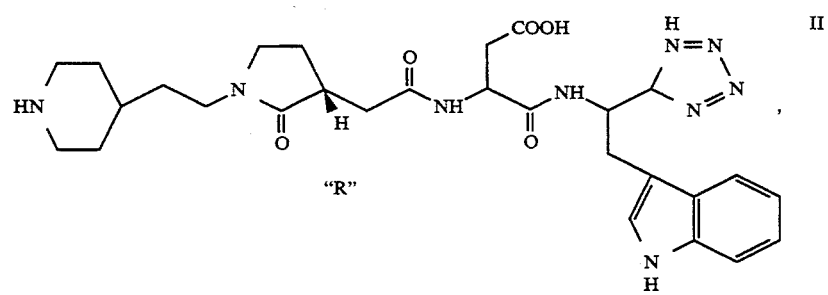

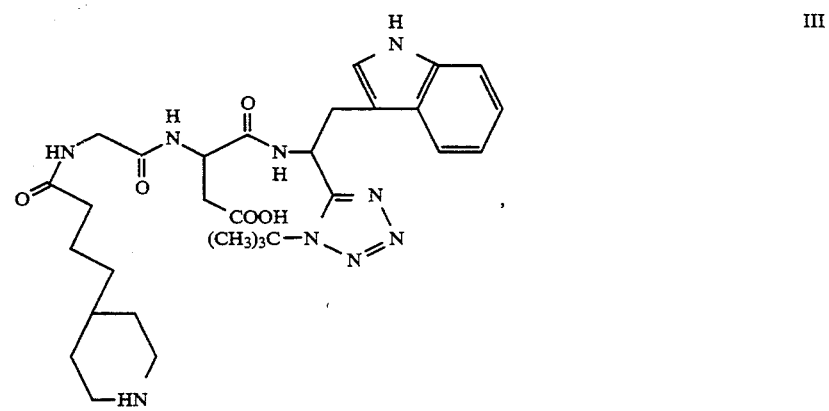

IV

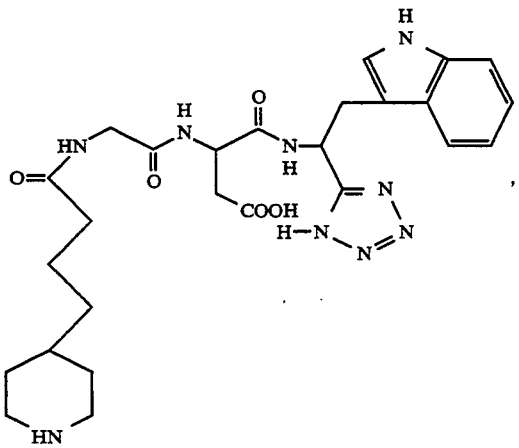

and

V

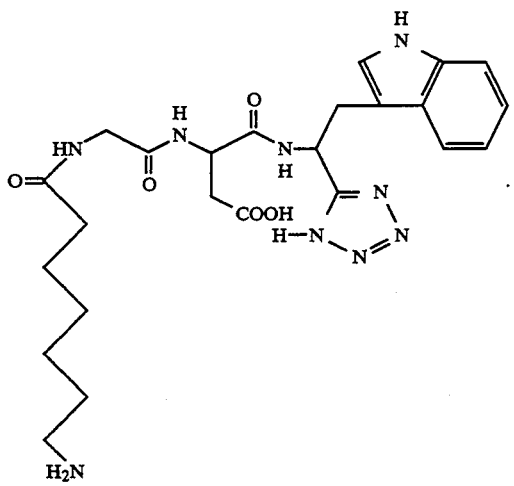

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include streptokinase and tissue plasminogen activator. The term "platelet anti-aggregation agent" shall include aspirin and dipyridamole.

The term "alkyl" means straight or branched alkane, alkene or alkyne.

The term "alkoxy" includes an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a $C_{1-6}$ alkyl substituted with $C_{1-6}$ alkylcarbonylamino is equivalent to

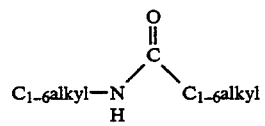

In the schemes and examples below, various reagent symbols have the following meanings:

BOC(Boc): t-butyloxycarbonyl
Pd/C: palladium on activated carbon catalyst
Cbz: carbobenzyloxy
$CH_2Cl_2$: methylene chloride
$CHCl_3$: chloroform
etch: ethanol.
MeOH: methanol.
EtOAc: ethyl acetate.
HOAc: acetic acid.
BOP: benzotriazol-1-yloxytris(dimethylamino)phosphonium, hexafluorophosphate.
EDC: 1-(3-Dimethylaminopropyl)-3-ethylcarbodiimide
Oxone: potassium peroxymonosulfate
LDA: lithium diisopropylamide
Ind: indole
Aha: amino heptanoic acid
DIEA: diisopropylethylamine
HOOBt: 3,4-dihydro-3-hydroxy-4-oxo-1,2,3-enzotriazine
t-Bu: tert-butyl
Pib: 4-piperidine butyryl
TFA: trifluoroacetic acid
[CHN4]: tetrazole As mentioned, compounds of the invention, by virtue of a tetrazole group replacing a C-terminal carboxyl group are less susceptible to metabolism by certain proteases present in the GI tract as well as elsewhere in the body. The compounds show in vivo activity after oral administration as a consequence of this increased metabolic stability.

Administration

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but nontoxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and clotting. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 1.0–100 mg/kg/day and most preferably 1–20 mg/kg/day. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or careers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-coagulation agents or thrombolytic agents such as plasminogen activators or streptokinase to achieve synergistic effects in the treatment of various vascular pathologies. They may also be combined with heparin, aspirin, or warfarin.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

In addition to the following preparative procedures, several examples of in-vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

In vitro platelet aggregation is measured at 37° C. in a Chronolog aggregometer. The reaction mixture contains gel-filtered human platelets ($2 \times 10^8$ per ml), fibrinogen (100 micrograms per ml ($\mu$g/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The following compounds of the invention were evaluated by the above-described assay.

| Compound | $IC_{50}$ $\mu M$ |
|---|---|
| V | 0.084 |
| IV | 0.024 |
| III | 0.024 |
| I | 0.13 |
| II | 0.011 |

In vivo activity of compounds of the present invention was measured in dogs according to the following procedure whereby dogs were administered an oral solution of the compound to be tested in aqueous solution. Blood samples were withdrawn at various times and platelet rich plasma was prepared. The ability of the platelets to aggregate in response to ADP or collagen was measured, and is reported as the percent inhibition relative to a control sample of platelets removed from the same animal prior to drug administration.

Compound IV showed dose-dependent inhibition of ex vivo platelet aggregation following oral administration to dogs at doses from 0.2–2 mg/kg. At 0.2 mg/kg, essentially no inhibition of ADP- or collagen-induced aggregation was seen. At doses of 1 or 2 mg/kg, 90–100% inhibition was elicited at 40 minutes–1.5 hours after oral dosing. Platelet aggregation returns to normal by 8 hours post-dosing. Compound III elicited modest inhibition of ex vivo platelet aggregation following oral administration at 1 or 2 mg/kg (20–35% inhibition). Compound II showed 50–75% inhibition at 1-2 hours following oral administration of 0.2 mg/kg. Activity returned to base line by 5 hours after oral administration.

This example describes procedures for preparing three specific compounds falling within the scope of the present invention.

EXAMPLE 1

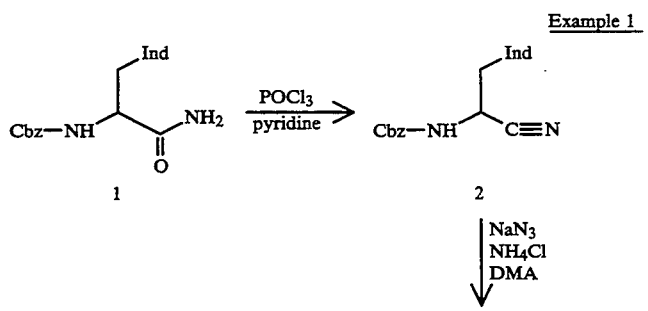

Example 1

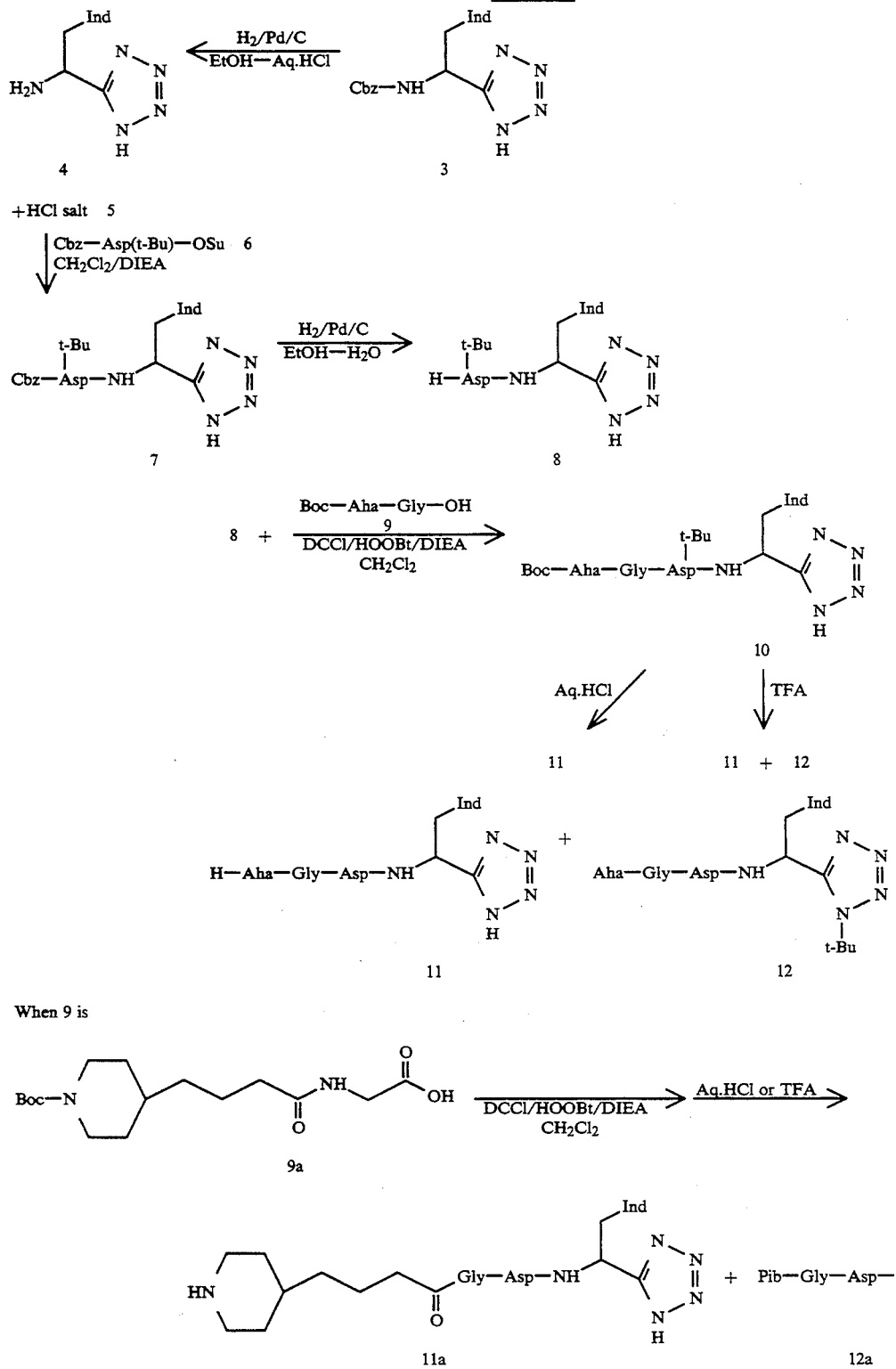

-continued
Example 1

Cbz-Trp ψ-[CN] (2)

A suspension of Cbz-Trp-NH$_2$ (1.69 g, 5 mmol) in pyridine (6.2 ml) was cooled to 0° C. and phosphorylchloride (0.625 ml, 6.83 mmol) was added dropwise with magnetic stirring. After 1 hr. at 0° C., ice-water (25 ml) was added and the reaction mixture was stirred for an additional 30 min. The solid was filtered, washed with water and dried in vacuo to give the nitrile product (1.473 g, 92.3%).

Anal. for C$_{19}$H$_{17}$N$_3$O$_2$ calcd. C, 71.45; H, 5.37; N, 13.16; Fd. C, 71.14H, 5.24, N, 13.09;

TLC (silica gel), Rf 0.7 (95-5, CHCl$_3$-MeOH).

Cbz-Trp ψ-[CHN₄] (3)

To a solution of Cbz-Trp ψ-[CN] (1.28 g, 4 mmol) in DMA (3 ml) was added sodium azide (0.288 g, 4.4 mmol) and ammonium chloride (0.236 g, 4.5 mmol). The resultant suspension was stirred magnetically and heated to 90°-95° C. for 6 hrs. Additional mounts of NaN₃ (0.287 g) and NH₄Cl (0.236 g) were added and the mixture was kept at 90°-95° C. for an additional period of 6.5 hrs. The reaction mixture was cooled to 25° C. and the solvent was evaporated in vacuo. The residue was triturated at 0° C. with 1 NHCl (10 ml) and the resultant solid was filtered, washed with water and dried in vacuo to give the tetrazole product (1.383 g, 95.4%)

Anal. for $C_{19}H_{18}N_6O_2$ calcd. C, 62.97, H, 5.01, N, 23.19; fd. C, 62.56, H, 4.80, N, 22.66;

TLC (silica gel), Rf 0.25 (80-20-2, CHCl₃-MeOH-con.NH₄OH).

Trp ψ-[CHN₄] (4+5)

A suspension of Cbz-Trp ψ-[CHN₄] (1.27 g, (3.5 mm) in ethanol (25 ml), 1N HCl (1.0 ml) and 10% Pd/C (250 mg) at 25° C. was treated with H₂ at atmospheric pressure with magnetic stirring. After 10 hrs, the reaction mixture was filtered through a pad of Celite, followed by washing the catalyst/Celite pad with several portions of ethanol. The filtrate was evaporated in vacuo to give a thick oil which was triturated with water. The resultant solid was filtered, washed with water and dried in vacuo to give product as zwitterion 4 (0.4853 g, 60.75%). The filtrate was lyophilized to give additional product as the HCl salt 5 (0.36 g, 38.85%).

TLC (silica gel), Rf 0.22 (70-30-3, CHCl₃-MeOH-conNH₄OH).

Cbz-Asp (t-Bu)-Trp ψ-[CHN₄] (7)

To a suspension of 4 and 5 (0.45 g, 1.97 mmol zwitterion and 0.35 g, 1.32 mmol of hydrochloride salt) in CH₂Cl₂ (16 mL) was added with magnetic stirring Cbz-Asp (t-Bu)-hydroxy succinimide ester (6) (1.513 g, 3.74 mmol) and diisopropyl ethylamine (DIEA) (0.4 mL). The reaction mixture was stirred magnetically at 25° C. retaining the pH at 7.0-7.2 (moist pH paper) by periodic addition of DIEA (1.15 mL). After 5 h, saturated NaHCO₃ solution (10 mL) and CH₂Cl₂ (20 ml) were added, the layers were separated and the CH₂Cl₂ layer was extracted with three additional portions of aqueous NaHCO₃ solution, followed by extraction with 2 portions of KHSO₄ (pH2) solution, and 1 portion of saturated NaCl. The organic layer was dried with MgSO₄, filtered and evaporated in vacuo to constant weight (1.82 g).

TLC (silica gel) Rf 0.65 (70-30-3, CHCl₃-MeOH-conNH₄OH).

H-Asp (t-Bu)-Trp ψ-[CHN₄] (8)

To a solution of 7 (1.75 g, 3.28 mmol) in aqueous ethanol (1:10, 22 mL) was added 10% Pd/C (0.5 g) and the suspension was treated with H₂ at atmospheric pressure with magnetic stirring for 5 h. The reaction mixture was filtered through a pad of Celite, and the filtrate was evaporated in vacuo to an oily residue (1.38 g). The residue was triturated with H₂O at 0° C. and the resultant solid was filtered to give the deprotected product 8 (0.8142 g, 62%). The filtrate was evaporated to a small volume from which a second crop of 8 (0.171 g, 13.1%) was obtained.

TLC (silica gel) Rf=0.4 (70-30-3, CHCl₃-MeOH-con.NH₄OH).

Boc-Aha-Gly-Asp(t-Bu)-Trp ψ-[CHN₄] (10)

To a suspension of Boc-Aha-Gly-OH (9) (0.0907 g, 0.3 mmol), 3,4-dihydro-3-hydroxy-4-oxo-1, 2, 3-benzotriazine (HOOBt, 0.049 g, 0.3 mmol) in CH₂Cl₂ (2 mL) was added with magnetic stirring a 0.5M solution of DCCI in CH₂Cl₂ (0.575 mL, 0.2875 mmol). After stirring for 8 min, 8 (100 mg, 0.25 mmol) was added and the pH of the suspension was adjusted to 7.2 (moist pH paper) with DIEA (0.093 mL). After 40 min, additional CH₂Cl₂ (50 mL) and aqueous NaHCO₃ solution (10 mL) was added. The organic layer was extracted 3 times with saturated bicarbonate solution and 2 times with KHSO₄ solution (pH 2). The CH₂Cl₂ layer was dried with MgSO₄, filtered and evaporated to an oil (0.16 g, 94%) which solidified upon standing.

TLC (silica gel) Rf 0.7 (70-30-3, CHCl₃-MeOH-conc.NH₄OH); HPLC (C₁₈) t=19.66 min, 94.8% pure by AUC@210 nm, 95% A TO 5% A over 30 min, solvent A=99.9% H₂O-0.1% TFA, solvent B=99.9% CH₃CN-0.1% TFA).

H-Aha-Gly-Asp-Trp ψ-[CHN₄] (11) and H-Aha-Gly-Asp-Trp ψ-[CN₄]-t-Bu (12)

A solution of 10 (150 mg, 0.219 mmol) in TFA containing 1% DTE (2 mL) was kept at 25° for 1 h. Ether (50 mL) and petroleum ether (25 mL) were added which precipitated the product mixture of 11 and 12 as a gum. Chromatography using a C₁₈ Delta Pak 5×30 cm column and eluting with a gradient of 95% A-B to 30% A-B over 60 min. at a rate of 80 mL/min (A=99.6% H₂O-0.4% HOAc, B=99.6% CH₃CN-0.4% HOAc) yielded product 11 (50.8 mg, 44%) and product 12 (28.3 mg, 23%) of >97% purity as measured by HPLC (C₁₈), AUC@210 nm, t=10.96 min (11), t=14.53 min (95% A to 5% A over 30 min. gradient, A=99.9% H₂O-0.1% TFA, B=99.9% CH₃CN-0.1% TFA;

NMR (D₂O) (11) 1.3 (m, 4H, Aha), 1.6 (m, 4H, Aha), 2.3 (t, 2H, Aha), 2.4 (dd, 1H, Asp β), 2.55 (dd, 1H, Asp β), 2.9 (t, 2H, Aha), 3.45 (m, 2H, Trp β), 3.85 (s, 2H, Gly), 4.6 (dd, 1H, Aspd) 5.55 (s, 1H, Trp a 7.1, 7.25, 7.5 (s+t, t, d, 2, 1, 2H, Trp arom) by AUC@210 nm, 95% A to 5% A over 30 min, solvent A=99.9% H2O-9.1% TFA, solvent B=99.9% CH₃CN-0.1% TFA)

NMR (D₂O)(12) 1.3 (m, 2H, Aha), 1.55 (s, 9H, tBu) 1.6 (m, 2H, Aha), 2.3 (2, 2H, Aha), 2.5 (dd, 1H, Asp b), 2.6 (dd, 1H, Asp b), 2.92 (t, 2H, Aha), 3.45 (m, 2H, Trp b), 3.9 (s, 2H, Gly), 4.63 (m, 1H, Asp a) 5.45 (t, 1H, Trp a) 7.08, 7.2, 7.48 (t, m, d, 1H, 3H, 1H, Trp arom).

AAA after 20 h hydrolysis with methane sulfonic acid;

11: Asp (1) 1.04, Gly (1) 1.06, Aha (1) 0.90;
12: Asp (1) 1.04, Gly (1) 1.06, Aha (1) 0.89.

Pib-Gly-Asp-Trp ψ-[CHN₄] (11a) and Pib-Gly-Asp-Trp ψ-[CN₄]-t-Bu (12a)

8 was reacted with 9a and deblocked with anhydrous TFA to give 11a and 12a. Aqueous HCl deblocking of the protected derivative gave 11a as the only product. 11a:

NMR (DMSO-d₆) 1.3 (m, 4H, Pib), 1.54 (m, 3H, Pib), 1.72 (m, 2H, Pib) 2.13 (t, 2H, Pib), 2.48 (dd, >1H, Asp b+DMSO), 2.63 (dd, 1H, Asp b), 2.78 (m, 2H, Trp b)

3.17 (m, >2H, Pib, H2O), 3.48 (dd, 1H, Gly a)

3.75 (dd, 1H, Gly a), 4.55 (9, 1H, Asp a), 5.35
(g, 1H, Trp a) 6.88, 6.93, 7.01, 7.28, 7.47
(d, t, t, d, d, 5H, Trp arom.), 8.0, 8.08, 8.14
(d, d, t, 3H, amide NHs), 10.63 (d, 1H, Indole NH)
FABMS: M+H=554.4 (calc.m.wt. 553.6) 12a:
NMR (DMSO.d$_6$): 1.5 (s, 9H, t-Bu), 6.83, 6.95, 6.99,
 7.22 (t, t, d, d, 1, 1, 1, 2 Hs, Trp arom), 10.74 (bs,
 1H, Ind NH)
FABMS: M+H=610.4 (calc.m.wt. 609.7)

EXAMPLE 2

Synthesis of Boc-Aha-Gly-OH (9)

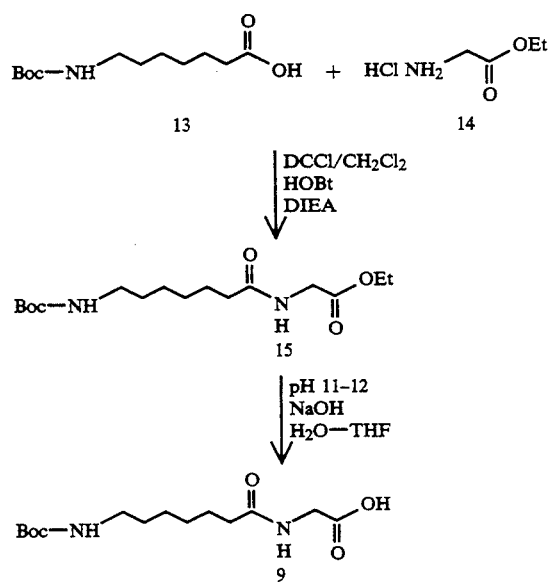

This example provides a description of a procedure for preparing Boc-Aha-Gly-OH, which is used for preparing compounds described in Example 1.

Boc-Aha-Gly-OEt (15)

To a suspension of HCl•Gly-OEt (14) (7.1 g, 50.8 mmol), Boc-Aha-OH (13), 13.26 g, 54.3 mmol), HOBt.-H$_2$O (8.415 g, 15 mmol) in CH$_2$Cl$_2$ (100 ml) was added with magnetic stirring DIEA (7 mL) and 0.5M DCCI in CH$_2$Cl$_2$ (110 mL, 55 mmol). The pH was kept at 7.2 (moist pH paper) by addition of DIEA (13.5 mL) over a period of 1 hr. After 2 hrs. at 25° C., the reaction mixture was filtered and the filtrate was extracted with 3× saturated NaHCO$_3$ solution and with 3×1N KHSO$_4$ solution. The organic layer was dried with anh. MgSO$_4$. After filtration and evaporation of solvent, the residue was crystallized from ether-petroleum ether to give product 15 (14.74 g, 88%)

Analysis calcd. for C$_{16}$H$_{30}$N$_2$O$_5$ C, 58.16, H, 9.15, N, 8.48; found C, 58.05, H, 9.07, N, 8.50.

TLC (silica gel) Rf=0.5 (95-5; CHCl$_3$-MeOH) NMR (CDCl$_3$): 1.3 (t, 3H, Et), 1.35 (m, 4H, Aha) 1.45 (m+s, 9H, tBu, Aha), 1.67 (m, 2H, Aha) 2.22 (t, 2H, Aha), 3.1 (m, 2H, Aha), 4.03 (d, 2H, Gly), 4.22 (9, 2H, Et), 4.5 (s, 1H, NH), 6.0 (s, 1H, NH)

FABMS M+H=331.3 (calc.m.wt.=330.4)

Boc-Aha-Gly-OH (9):

A suspension of Boc-Aha-Gly-OEt (15) (6.6 g, 20 mmol) in 25% THF in H$_2$O (200 mL) was adjusted to pH 11.3 with 2.7N NaOH with magnetic stirring. The pH of the reaction mixture was kept at 11–11.5 by periodic additions of NaOH. After base uptake ceased (6 hrs.), ether (300 mL) was added, the layers were separated and the organic layer was extracted with two portions of H$_2$O. The volume of the combined aqueous layers was reduced to 150 mL and the solution was a acidified to pH 2.8 with KHSO$_4$ and extracted with 3 portions (150 mL) of ether. The organic layers were dried with MgSO$_4$, filtered and evaporated to an oil (6.52 g). The product was crystallized from EtOAc-petroleum ether to give 9 ( 5.27 g, 87.1% )

Analysis calc. for C$_{14}$H$_{26}$N$_2$O$_5$: C, 55.61, H, 8.67, N,.9.27, found C, 55.47, H, 8.77, N, 9.25

TLC (silica gel) Rf 0.15 (80-20-2, CHCl$_3$-MeOH-conc.NH$_4$OH)

NMR (CD$_3$OD) 1.35 (m, 4H, Aha) 1.45 (m+s, 11H, t-Bu+Aha) 1.63 (m, 2H, Aha), 2.25 (t, 2H, Aha) 3.05 (t, 2H, Aha), 3.9 (s, 2H, Gly)

FABMS M+H=303.2 (calc.m.wt.302)

EXAMPLE 3

Synthesis of Boc-Pib-Gly-OH (9a)

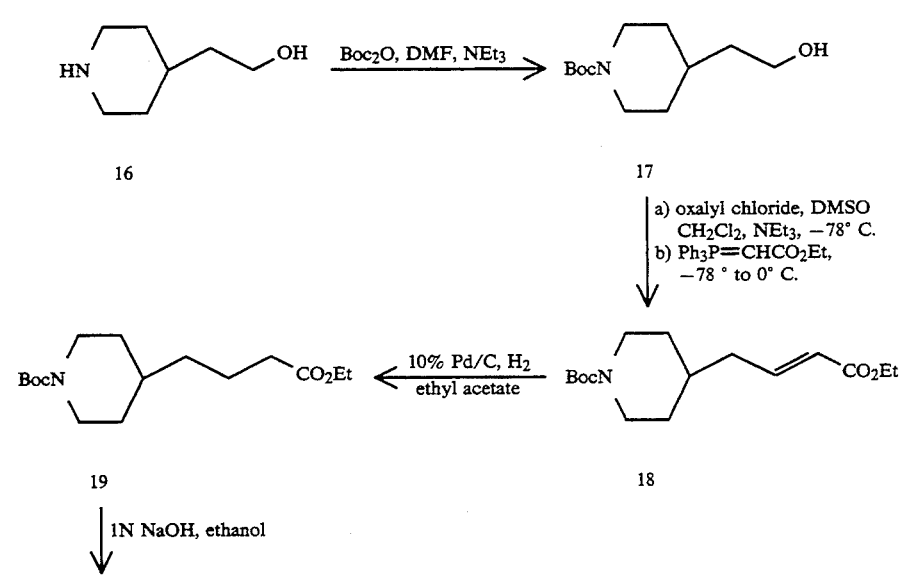

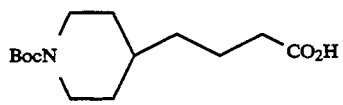

20

| as in Example 2
substituting 20 for 13

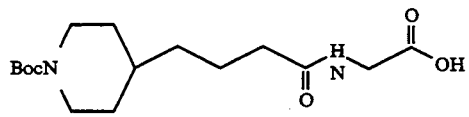

9a

This example provides a description of a procedure preparing Boc-Pib-Gly-OH, which is used for preparing compounds described in Example 1.

Preparation of N-Boc-4-piperidineethanol (17)

To a stirred solution of 4-piperidine-ethanol (16) (18.7 g, 0.14 mol) and DMF (200 mL) at 0° C. was added N-tert-butoxoycarbonyl anhydride (31 g, 0.14 mmol). After 1.0 hour the cooling bath was removed and the reaction mixture stirred for 20 hours. The reaction mixture dried (MgSO$_4$), and concentrated to furnish 17 (26 g) as a colorless oil.

TLC R$_f$=0.25 (40% ethyl acetate/hexanes);
$^1$H NMR (CDCl$_3$) d 4.09 (bs. 2H), 3.72 (t, J=7 Hz, 2H) 2.70 (m, 2H), 1.75-1.10 (m, 7H), 1.46 (s, 9H).

Preparation of Ethyl
4-(N-Boc-4-piperidyl)trans-crotonate (18)

To a stirred solution of oxalyl chloride (0.43 mL, 5.0 mmol) in CH$_2$Cl$_2$ (20 mL) at −78° C. was added DMSO (0.52 ml, 7.0 mmol) dropwise. After gas evolution subsided (∼5 minutes) the alcohol 17 (0.8 g, 3.5 mmol) in CH$_2$Cl$_2$ (20 mL) was added in a stream. After 20 minutes triethylamine (1.7 mL, 12 mmol) was added dropwise and then the cooling bath removed. After 20 minutes (carbethoxymethylene) triphenylphosphorane (1.4 g, 4.0 mmol) was added. After 2.0 hours the reaction mixture was diluted with petroleum ether and then washed sequentially with H$_2$O, 5% KHSO$_4$, and brine, dried (MgSO$_4$) and concentrated. Flash chromatography (silica, 15% ethyl acetate/hexanes) gave the ester 18 (0.57 g) as a colorless oil.

TLC R$_f$=0.79 (50% ethyl acetate/hexanes);

$^1$H NMR (CDCl$_3$)d 6.91 (dt, J=16 and 7 Hz, 1H), 5.81 (bd, J=17 Hz, 1H), 4.18 (q, J=7 Hz, 2H), 4.08 (m, 2H), 2.67 (m, 2H), 2.14 (t, J=7 Hz, 1.70-1.05 (m, 5H), 1.44 (S, 9H), 1.28 (t, J=7H, 3H).

Preparation of Ethyl 4-(N-Boc-4-piperidyl) butyrate (19)

The olefin 18 (26 g, 87 mmol) in ethyl acetate (500 ml) was hydrogenated, at ambient temperature, under a hydrogen atmosphere (1 atm) in the presence of 10% Pd/C (5.0 g) overnight. The reaction mixture was then purged with argon followed by filtration through a celite pad. Concentration of the filtrate followed by flash chromatography (silica, 10% ethyl acetate/hexanes) gave the ester 19 (24 g) as a crystalline solid.

TLC R$_f$=0.52 (20% ethyl acetate/hexanes); $^1$H NMR (CDCl$_3$)d 4.16 (q, J=7 Hz, 2H), 4.10 (m, 2H), 2.69 (m, 2H), 2.31 (t, J=7 Hz, 2H), 1.68 (m, 4H), 1.38 (s, 9H), 1.40 (m, 1H), 1.11 (m, 2H).

Preparation of 4-(N-Boc-4-piperidyl) butanoic acid (20)

A solution of ester 19 (19 g, 63 mmol), ethanol (300 mL) and 1N NaOH (100 mL, 100 mmol) was stirred at ambient temperature for 2.5 hours followed by concentration. The residue was diluted with 5% KHSO$_4$ and ethyl acetate and transferred to a separatory funnel. The phases were shaken then separated and the organic portion was washed with brine, dried (MgSO$_4$), and concentrated to give the acid 20 (18 g) as a colorless oil that crystallized upon standing.

TLC R$_f$=0.68 (ethyl acetate).

EXAMPLE 4

R and S Enantiomers of

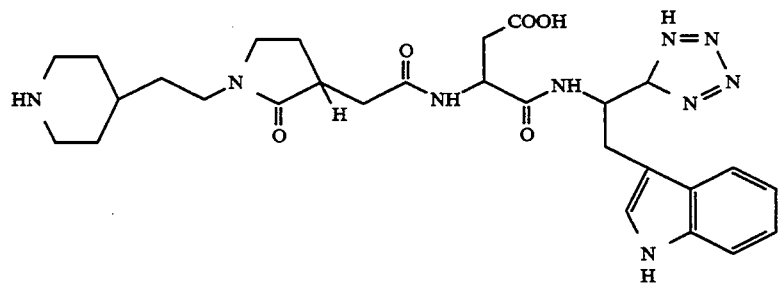

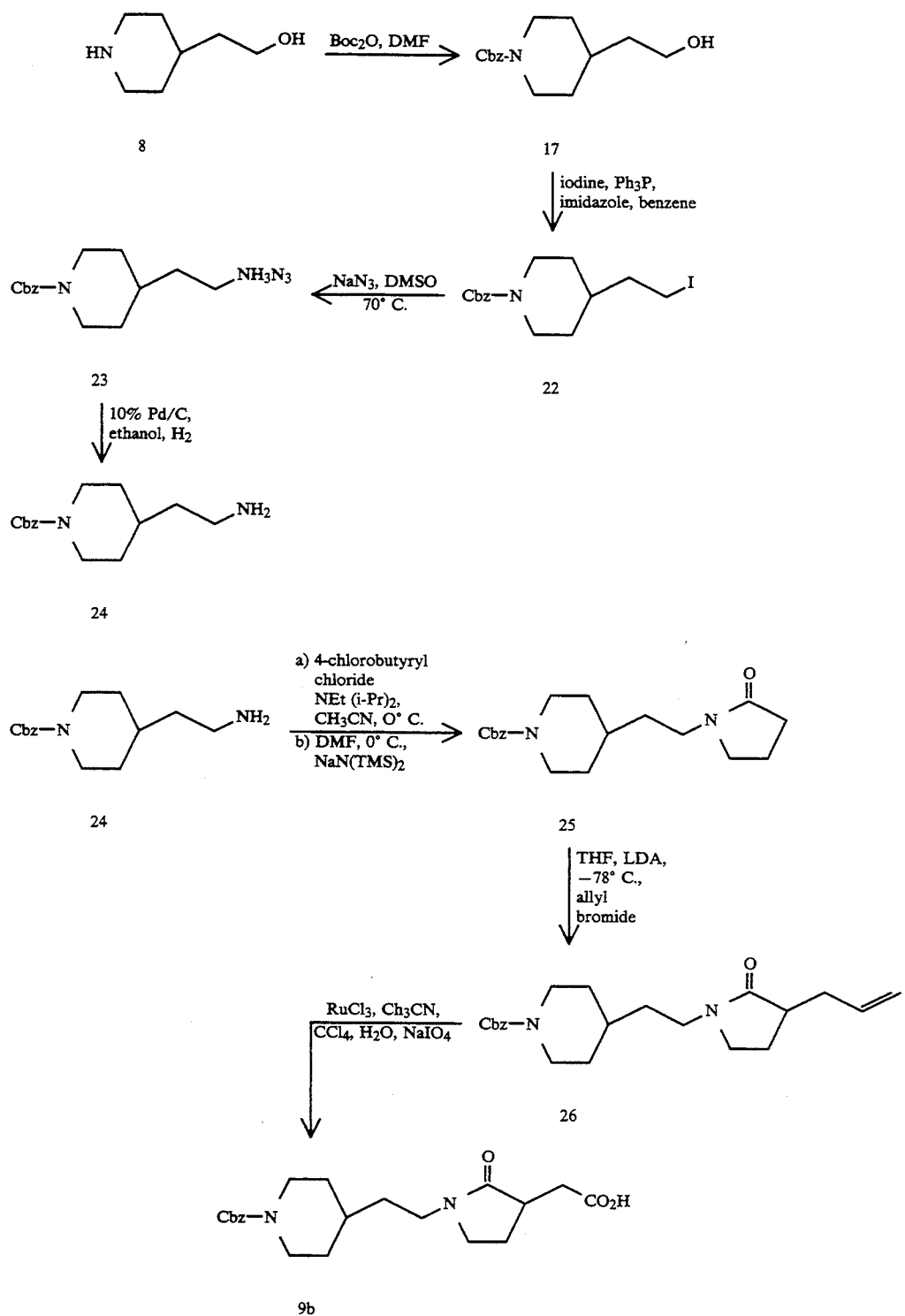

Preparation of N-Cbz-4-piperidine ethyl iodide (22).

To a stirring solution of 17 (18.0 g, 77 mmol), triphenylphosphine (22.2 g, 85 mmol), imidazole (7.9 g, 115 mmol), and benzene (800 mL) at ambient temperature was added iodine (22.0 g, 85 mmol). After 5 min the heterogeneous reaction mixture was filtered and the filtrate concentrated. Flash chromatography (silica gel, 10% ethyl acetate/hexanes) gave 22 (20 g, 59%) as an oil.

Preparation of N-Cbz-4-piperidine ethyl azide (23)

A solution of 22 (5.0 g, 14.7 mmol), DMSO (75 mL), and NaN$_3$ (1.9 g, 29.4 mmol), was heated at 70° C. for 2 hr. The cooled reaction mixture was diluted with ethyl acetate and then washed with water (2×) and brine, dried (MgSO$_4$), and concentrated to afford 23 (3.6 g, 96%) as a colorless oil.

Preparation of N-Cbz-4piperidine ethyl amine (24)

A mixture of 23 (1.1 g, 4.3 mmol), 10% Pd/C (0.16 g), and ethanol was stirred under a hydrogen atmosphere (1 atm) for 1.5 hr. The reaction mixture was then filtered through a celite pad and the filtrate concentrated to give crude 24 (1.0 g) as an oil.

Preparation of 1-[2-(N-Cbz-piperidin-4-yl)ethyl]-(2-pyrrolidinone (25)

To a stirred solution of 24 (2.7 g, 11.8 mmol) acetonitrile (60 mL), and diisopropyl ethylamine (4.1 mL 23.6 mmol) at 0° C. was added 4-chlorobutyryl chloride (2.6 mL, 23.6 mmol) followed by removal of the cooling bath. After 5 hr the reaction mixture was diluted with ethyl acetate and then washed with water (2×) and brine, dried (MgSO4), and concentrated. The crude amide was dissolved in DMF (60 mL) cooled to 0° C. then treated with NaN(TMS)2 (1M in THF, 11.8 mL). After 5 min the reaction mixture was diluted with ethyl acetate and then washed with water and brine, dried (MgSO4), and concentrated. Flash chromatography (silica gel, 50% ethyl acetate/hexanes); gave 25 (0.4 g, 12%) as a colorless oil.

Preparation of 1-[2-(N-Cbz-piperidin-4-yl)ethyl]-3-propen-2yl-(2-pyrrolidinone) (26)

To a stirred solution of 25 (325 mg, 1.1 mmol) in THF (5 mL) at −78° C. was added LDA (0.5M in THF 2.4 mL) dropwise. After 15 min allyl bromide (0.16 mL, 2.2 mmol) was added and the reaction stirred at −78° C. for 1 hr followed by quenching with HOAc (0.1 mL). The reaction mixture was then diluted with ethyl acetate and then washed with water and brine, dried (MgSO4), and concentrated. Flash chromatography (silica gel, 50% ethyl acetate/hexanes) gave 26 (160 mg, 45%) as an oil.

Preparation of 1-[2-(N-Cbz-piperidin-4-yl)ethyl]-(3-acetic acid-2-pyrrolidinone (9b)

To a vigorously stirred solution of 26 (130 mg, 0.4 mmol), CCl4, acetonitrile, and water at ambient temperature was added RuCl3 and excess NaIO4. After 60 hr the reaction was filtered through a celite pad washing with ethyl acetate. The filtrate was extracted with sat. NaHCO3 followed by acidifying the aqueous phase to pH 3 with 5% KHSO4. The acidic aqueous phase was then extracted with ethyl acetate (2×) and the organic portion was dried (MgSO4) and concentrated. Flash chromatography (silica gel, 9:0.2:0.2 CH2Cl2/CH3OH/HOAc) gave 27 (80 mg, 48%) as an oil.

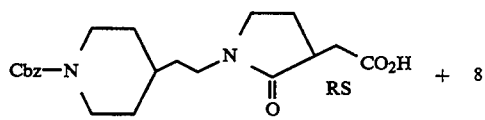

9b          + 8

↓

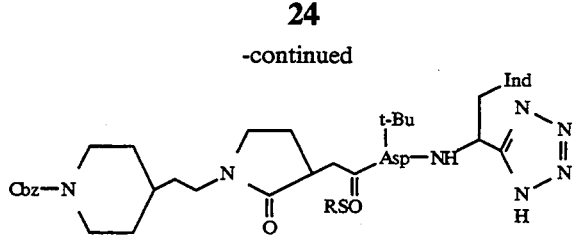

10b

1) H2/Pd/C
2) aqueous HCl

↓

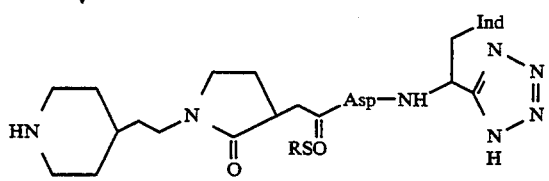

11b-I  (S)
11b-II (R)

Coupling to give (10b)

To a suspension of 9b (766 mg, 1.97 mmol) and HOOBt (3,4-Dihydro-3-hydroxy-4-oxo-1, 2, 3-benzotriazine, 366 mg, 2.06 mmol) in CH2Cl2 (16 mL) was added a 0.5M DCCl/CH2Cl2 solution (3.90 mL, 1.95 mmol) and the reaction mixture was stirred magnetically at 25° C. for 5 min after which time period a homogeneous solution was obtained. The dipeptide 8 (780 mg; 1.95 mmol) and additional CH2Cl2 (4 mL) were added and the pH of the reaction mixture was adjusted to 7.3 with DIEA (0.76 mL). After 2 h at 25° C., H2O (10 mL) was added and the mixture was stirred magnetically for 30 min. Additional CH2Cl2 (10 mL) was added, the reaction mixture was filtered, the filtered solids were washed with CH2Cl2 (15 mL) and layers of the filtrate were separated. The organic layer was washed 3 times with H2O (10 mL each), once with dilute aqueous KHSO4 solution pH 2-3, once with saturated NaCl solution, filtered and dried with MgSO4. After filtration, the filtrate was evaporated in vacuo to give product (1.32 g).

HPLC 95% A/B to 5% a/B in 30 min, retention times 19.04' and 19.44' in equal proportions. A=0/1% TFA/H2O; B=0.1% TFA/CH3CN

Deblocking of (10b) in 2-step procedure to give (11b-I) and (11b-II)

STEP 1

A suspension of 10b (1.3 g) in HOAc-H2O (2:1 v/v, 45 mL) was treated with 10% Pd/C (0.9g) and H2 gas at atmospheric pressure for 20 h with magnetic stirring. The mixture was filtered through a pad of Celite under N2, and the filtrate was evaporated in vacuo to an oily residue which was diluted with water and lyophilized to give the des-Cbz product of 10b (0.97 g).

HPLC analysis showed 2 peaks with retention times 18.59' and 19.20' in equal amounts; gradient 95% A/B to 50% A/B in 30 min; A-0.1% TFA-H2O, B=0.1% TFA-CH3CN.

STEP 2

The crude product (0.97 g) from the hydrogenation reaction was dissolved in H2O (5 mL) and 6N HCl (18 mL) was added over a period of 4.5 h with magnetic stirring. After an additional 1.5 h at 25° C., the reaction solution was neutralized to pH 7.5 with NH₄OH (17 mL). The reaction solution contained product as the two diastereomers at the lactam-3 carbon; HPLC: retention times 13.93' (11b-I) and 14.24' (11b-II), gradient 90% A/B to 75% A/B in 30 min: A=0.1% TFA-H₂O, B=0.1% TFA-CH₃CN.

The two isomeric products were separated by repeated reserve phase HPLC using a Deltic Pak C₁₈, 15 m, 300 Å column and eluting with a gradient solvent of 95% A/B to 82% A/B in 60 min, A=0.1% TFA-H₂O, B=0.1% TFA-CH₃CN. Fractions containing the isomers 11b-I and 11b-II in >90% purity were combined and lyophilized to give 11b-I (120.6 mg) with peptide content of 1.34 mmol/mg as determined by elemental analysis, and FABMS M+H=580 (calcd mwt. 579.6); and 11b-II (85 mg) with peptide content of 1.34 mmol/mg as calculated from elemental analysis, and FABMS: M+H=580 (calc. mwt. 579.6).

Therapeutic Treatment

Compounds of the invention may be used for inhibiting integrin protein-complex function relating to cell attachment activity. They may be administered to patients where inhibition of human or mammalian platelet aggregation or adhesion is desired.

Compounds of the invention are eliminated from circulation rapidly and are particularly useful in inhibiting platelet aggregation in situations where a strong antithrombotic of short duration or effectiveness is needed. Thus, they may find utility in surgery on peripheral arteries (arterial grails, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. A compound having the formula

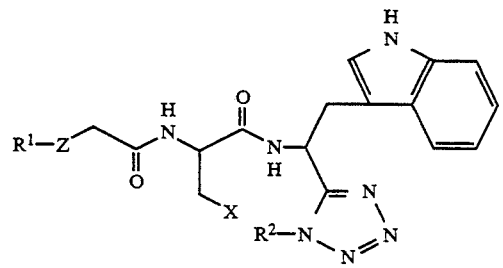

wherein Z is

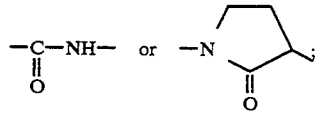

X is COOH;

R¹ is Y—R³, wherein R³ is a C₁-C₆ alkyl and Y is amino or piperidinyl; and

R² is H or a C₁-C₄ alkyl and pharmaceutically acceptable salts thereof.

2. A compound of claim 1 selected from the group consisting of

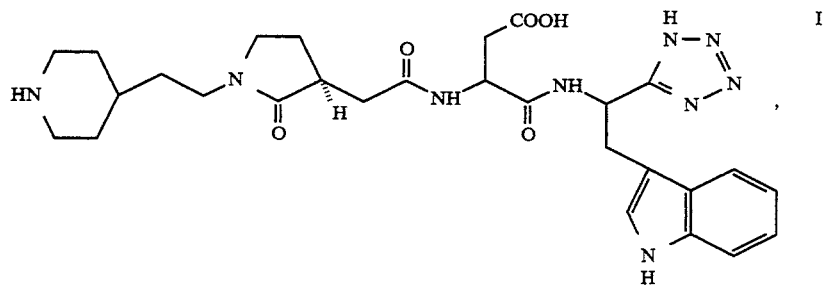

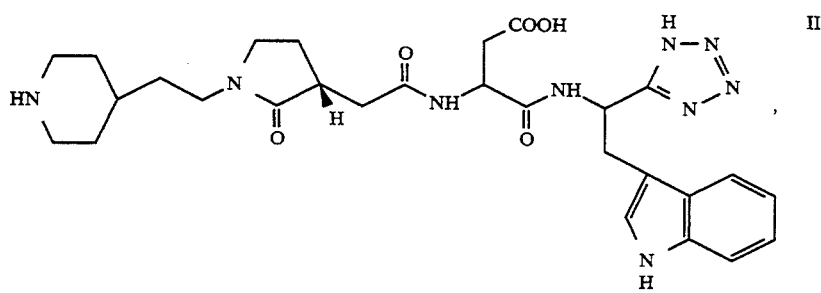

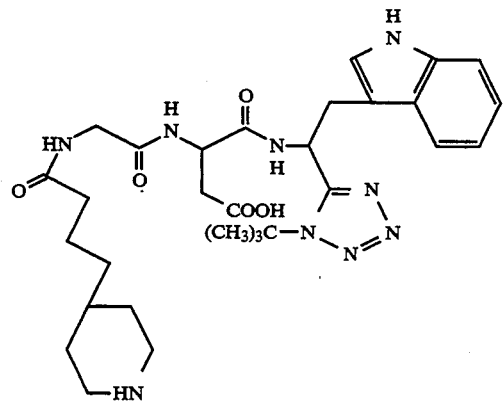
III
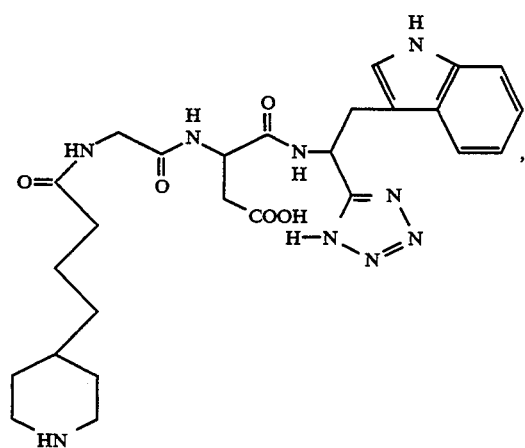
IV
and
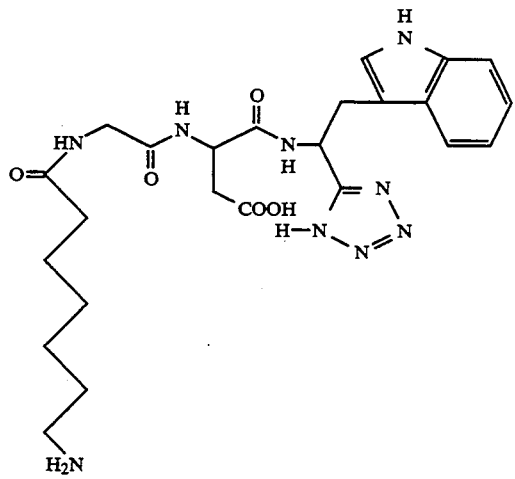
V
3. A composition for inhibiting the aggregation of blood platelets in a mammal, comprising a compound of claim 1 and a pharmaceutically acceptable carrier.
4. A method for inhibiting the aggregation of blood platelets in a mammal, comprising administering to the mammal a composition of claim 3.
* * * * *